United States Patent [19]

Matsuura et al.

[11] Patent Number: 5,169,767
[45] Date of Patent: Dec. 8, 1992

[54] METHOD OF PRODUCING TREHALOSE

[75] Inventors: Kazuho Matsuura, Kyoto; Reiko Shigemoto, Muko, both of Japan

[73] Assignee: Takeda Chemical Industries, Ltd., Osaka, Japan

[21] Appl. No.: 801,616

[22] Filed: Nov. 27, 1991

Related U.S. Application Data

[63] Continuation of Ser. No. 521,727, May 8, 1990, abandoned.

[30] Foreign Application Priority Data

Jun. 5, 1989 [JP] Japan .................................. 1-143609

[51] Int. Cl.$^5$ .................. C12P 19/12; C12P 19/44; C12N 1/38; C12N 1/12
[52] U.S. Cl. ........................... 435/100; 435/74; 435/244; 435/252.1; 435/822; 435/254; 435/911
[58] Field of Search ............. 435/74, 100, 244, 252.1, 435/822, 254, 911

[56] References Cited

U.S. PATENT DOCUMENTS 4,011,391  3/1977  Horii et al. .......................... 536/17
4,089,947  5/1978  Horii et al. .......................... 424/181

FOREIGN PATENT DOCUMENTS 50-154485  12/1975  Japan .
58-216695  12/1983  Japan .

OTHER PUBLICATIONS

The Journal of Antibiotics, vol. XL, No. 4, Apr. 1987, "Effect of Validamycins on Glycohydrolases of Rhizoctonia Solani", Naoki Asano et al., pp. 526-532.

Primary Examiner—Douglas W. Robinson
Assistant Examiner—Michael V. Meller
Attorney, Agent, or Firm—Wegner, Cantor, Mueller & Player

[57] ABSTRACT

The present invention provides a method for producing trehalose, which comprises culturing microorganisms capable of producing trehalose, in a culture medium containing validamycin or a derivative thereof.

18 Claims, No Drawings

METHOD OF PRODUCING TREHALOSE

This application is a continuation of United States application Ser. No. 07/521,727 filed May 8, 1990, now abandoned.

BACKGROUND OF THE INVENTION

1. Field of the Invention

This invention relates to a method for producing trehalose, which is useful as a stabilizer of pharmaceuticals and also widely useful in the field of food processing.

2. Description of the Prior Art

Trehalose is one of disaccharides widely distributed in natural products such as yeasts, mold, marine animals, seaweeds, etc. As the methods of obtaining this substance, there have been known, among others, methods comprising extraction from the above-mentioned natural products or fermentation by microorganisms which are capable of producing trehalose, e.g. those belonging to the genus Arthrobacter [Agricultural and Biological Chemistry 33 190, (1969)] or those belonging to the genus Nocardia (JPA 50-154485). These methods are hardly workable for mass-production or require a great deal of energy accompanied with complicated operations and equipment of a large scale so as to refine the products to such an extent as to make them safely usable as pharmaceuticals or foodstuff. The yield of trehalose in the method is unsatisfactorily low. There has been known another method which comprises converting maltose into trehalose by the aid of an enzyme such as maltosephosphorylase, trehalosephosphorylase or the like (JPA 58-216695). In this method, however, a relatively high cost is required for preparation of the enzymes, and no method of producing trehalose at low cost and also in a large amount has yet been established.

DESCRIPTION OF PREFERRED EMBODIMENTS

While taking these circumstances into consideration, the present inventors conducted an extensive study to find an industrially advantageous method of producing trehalose, they found that, by culturing microorganisms capable of producing trehalose, especially those belonging to the genus Rhizoctonia or Sclerotium on a medium supplemented with validamycin or a derivative thereof, the yield of trehalose was remarkably improved. The fact that validamycin and a derivative thereof thus serves to promote the production of trehalose has not yet been known. Furthermore, the present inventors have diligently studied to establish an industrially advantageous method for producing trehalose. Therefore, the present invention is based upon the above unexpected finding.

The present invention thus relates to a method of producing trehalose by culturing microorganisms, especially those belonging to the genus Rhizoctonia or the genus Sclerotium which are capable of producing trehalose, the characteristic feature of which lies in adding to the culture medium validamycin or a derivative thereof.

As the microorganisms to be employed in the method of the present invention there are particularly desirable those belonging to the genus Rhizoctonia or the genus Sclerotium which are capable of producing trehalose.

Examples of microbes belonging to the genus Rhizoctonia to be employed in the present invention include, among others, Rhizoctonia solani AG-1 (accession number IFO-30465), Rhizoctonia solani AG-2-2 (accession number IFO-32334, Hokkaido University in Japan 2-2 IIIB) and Rhizoctonia oryzae (accession number IFO-32335, Ministry of Agriculture, Forestry and Fisheries in Japan, Central Agricultural Experiment Station C-301), and examples of microorganisms belonging to the genus Sclerotium include, among others, Sclerotium oryzae sativae (accession number IFO-32333, do., Central Agricultural Experiment Station C-344), Sclerotium fumigatum (accession number IFO-32332, do., Central Agricultural Experiment Station C-146), and Sclerotium hydrophilum (accession number IFO-5293). The Institute for Fermentation Osaka is located at 17-85, Juso-honmachi 2-chome, Yodogawa-ku, Osaka 532, Japan.

Validamycin to be employed in the method of the present invention is widely used as antibiotic substance for agricultural use, which is constituted with validoxylamine and D-glucose. Examples of validamycin and a derivative thereof to be employed in the method of present invention include a compound of the formula (I)

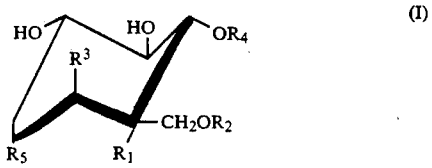

wherein $R_1$ is a hydrogen atom or a hydroxy group; $R_2$ is a hydrogen atom or a D-glucopyranosyl group; $R_3$ is a hydrogen atom or a hydroxy group; $R_4$ is a hydrogen atom, a D-glucopyranosyl group or a D-glucopyranosyl-D-glucopyranosyl group; $R_5$ is a hydrogen atom, an amino group or a substituent of the general formula

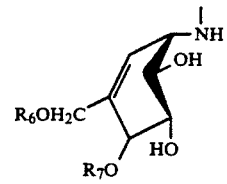

($R_6$ and $R_7$ are a hydrogen atom or a D-glucopyranosyl group), or (1S)-(1,4,6/5)-3-hydroxymethyl-4,5,6-trihydroxy-2-cyclohexenyl amine.

Among the compound of the formula (I) mentioned above, the following compounds are particularly desirably employed in the present invention.

| Validamycin derivative | $R_1$ | $R_2$ | $R_3$ | $R_4$ | $R_5$ | $R_6$ | $R_7$ |
|---|---|---|---|---|---|---|---|
| Validatol | H | H | H | H | H | — | — |
| Validamine | H | H | H | H | $NH_2$ | — | — |
| Valiolamine | OH | H | OH | H | $NH_2$ | — | — |

| Validamycin derivative | R₁ | R₂ | R₃ | R₄ | R₅ | R₆ | R₇ |
| --- | --- | --- | --- | --- | --- | --- | --- |
| Validoxylamine A | H | H | H | H | — | H | H |
| Validoxylamine B | H | H | OH | H | — | H | H |
| Validoxylamine G | OH | H | H | H | — | H | H |
| Validamycin A | H | H | H | β-D-Glc | — | H | H |
| Validamycin B | H | H | OH | β-D-Glc | — | H | H |
| Validamycin C | H | H | H | β-D-Glc | — | α-D-Glc | H |
| Validamycin D | H | α-D-Glc | H | H | — | H | H |
| Validamycin E | H | H | H | α-D-Glc(1-4)-β-D-Glc | — | H | H |
| Validamycin F | H | H | H | β-D-Glc | — | H | α-D-Glc |
| Validamycin G | OH | H | H | β-D-Glc | — | H | H |

Glc: Glucopyranosyl.

These compounds can be used singly or two or more of them can be used simultaneously.

In the present invention, the culture medium or culture broth of validamycin-producing microorganisms or its processed material, for example, is advantageously added without purification of validamycin or its derivatives to the culture medium of this invention.

The amount of validamycin or a derivative thereof to be added to a culture medium is in a range which does not inhibit the growth of the microorganisms then used, i.e. usually about 0.000001 to 0.01% (W/V), preferably about 0.00001 to 0.002% (W/V) relative to the whole culture medium.

The addition may be conducted in any manner, i.e. preliminary addition to the culture medium, and intermittent or continuous addition in the course of culturing.

Examples of nutritive sources to be used for the culture medium include carbon sources which the microorganisms can utilize, nitrogen sources, inorganic salts, organic acid salts and trace nutrients.

Examples of the carbon source include glucose, fructose, galactose, mannose, maltose, sucrose, lactose, glycogen, pectin, starch, etc., and any other carbon sources may be used so long as they can be utilized by the strains used.

Examples of nitrogen sources include various ammonium salts (ammonium sulfate, ammonium nitrate, ammonium chloride, ammonium phosphate), inorganic or organic nitrogen-containing substances such as corn steep liquor (hereinafter sometimes called CSL), peptone, meat extract, yeast extract, dry yeast, soybean flour, cotton seed cake, urea, etc.

As the inorganic salts, mention is made of such salts as those with potassium, sodium, calcium, magnesium, iron, manganese, cobalt, zinc, copper or phosphoric acid.

As the trace nutrients, use is suitably made of pantothenic acid, biotin, thiamine and riboflavin, other vitamins, L-cysteine and L-glutamic acid or natural products containing them.

The above-mentioned medium components may be previously added to the medium wholly, but they may also be added partly or wholly to the culture broth intermittently or continuously.

A culture medium which is known for culturing the above mentioned microorganisms can be used in the present invention.

The culture may be stationary, under shaking or under stirring with aeration.

Culture conditions vary, needless to state, with kinds of strains, composition of the medium for example, and they may be selected in individual cases so that the object product may be produced most efficiently. For example, the culture may be conducted preferably at about 25° C. to about 35° C., and pH of the medium is desirably about 5 to about 9.

By culturing for about 2 to 10 days under such conditions as described above, trehalose is accumulated in the culture medium or in the microorganisms at a high concentration. Incidentally, as the pH of the culture medium generally decreases in this case, it may be desirable to keep pH in the most suitable range constantly for the microbial production of trehalose by adding a suitable basic substance such as caustic soda, caustic potassium or ammonia, or to maintain the optimal pH by adding a suitable buffer to the culture medium.

The trehalose accumulated in the cell bodies thus cultured can be separated and purified by a per se known process.

Examples of the method for the separation and purification, include crushing, upon necessity, of dry mycelia and subjecting to extraction with about 10% (W/V) aqueous solution of trichloroacetic acid for several hours. The extract is subjected to filtration to remove solid matters, followed by removing lipid and trichloroacetic acid with chloroform and ether. The resultant is allowed to pass through an ion-exchange column to eliminate ionic substances, and the residue is subjected to evaporation to dryness, followed by dissolving it in acetonitrile or a mixture of acetonitrile and a suitable solvent (e.g. water, ethyl alcohol, acetone, etc.). This solution is subjected to chromatography (e.g. silica-gel chromatography, etc.) to isolate trehalose.

According to the present invention, trehalose can be produced easily and in a large amount.

WORKING EXAMPLES

By the following examples, the present invention will be described in more detail. The "%" used in the description of the culture media means weight/volume % (W/V %), unless otherwise specified. The seed culture medium is, unless otherwise specified, the potato sucrose agar medium (mixture of potato 200 g, sucrose 30 g, powdered yeast extract 2 g, agar 20 g and deionized water 1000 ml, abbreviated as PSA medium). The quantitative determination of trehalose was conducted by means of a high performance liquid chromatography under the conditions shown below.

| Conditions for determination by means of high performance liquid chromatography | |
| --- | --- |
| Device employed | LC-6A (Shimadzu Seisakusho Ltd.) |
| Column | Shim-pack CLC-NH₂ (aminopropyl group 5 μl, Shimadzu Seisakusho Ltd.) |
| Flow rate | 1.0 ml/min. |

| Conditions for determination by means of high performance liquid chromatography | |
| --- | --- |
| Mobile phase | 70% acetonitrile |
| Detector | differential refractometer |
| Retention time | trehalose: 12.5 min. |

EXAMPLE 1

100 ml of a modified Czapek's liquid culture medium (consisting of glucose 30 g, magnesium sulfate 0.5 g, sodium nitrate 2 g, potassium dihydrogenphosphate 1 g, iron sulfate 0.01 g and deionized water 1000 ml) was put into a 200 ml.-capacity flask, which was sterilized at 115° C. for 15 minutes. The resultant culture medium was inoculated with a piece of the growth (punched out with a cork borer, diameter 1 cm) of Rhizoctonia solani AG-1 (accession number IFO-30465) cultured on a potato sucrose agar (PSA) culture medium at 28° C. for two days, which was subjected to shake-culture at 28° C. for four days. Then the same experiment was carried out with the exception that validamycin A was added to the culture medium before the cultivating the medium, the amount of validamycin A being 0.005% relative to the whole culture medium. In each of the two experiments, the culture cells obtained thus above were respectively separated and purified, followed by subjecting to quantitative determination. As shown in Table 1, from the culture cells by culturing in the medium to which validamycin A was supplemented, a remarkably increased amount of trehalose was obtained as compared with those by culturing in the medium to which no validamycin A was supplemented.

TABLE 1

| | Influence of validamycin A of the production of trehalose | |
| --- | --- | --- |
| Amount of validamycin added (%) | Content of trehalose in mycelia (mg/g dry mycelia) | Ratio relative to control without validamycin A (%) |
| 0 | 63.9 | 100.0 |
| 0.0005 | 88.4 | 138.3 |

EXAMPLE 2

100 ml of a Czapek's liquid culture medium (consisting of sucrose 30 g, magnesium sulfate 0.5 g, sodium nitrate 2 g, potassium dihydrogenphosphate 1 g, iron sulfate 0.01 g and deionized water 1000 ml) put in a 200 ml.-capacity flask was sterilized at 115° C. for 15 minutes.

The resultant culture medium was inoculated with a piece of the growth (punched out with a cork borer, diameter 1 cm) of Rhizoctonia solani AG-1 (accession number IFO-30465) cultured on a PSA culture medium at 28° C. for two days and then subjected to shake-culture at 28° C. for four days. Two kinds of culture broth were prepared, one being cultured by supplemental addition of 0.0005% of validamycin A, and the other being cultured with no supplemental addition of validamycin A. The culture cells obtained thus above were respectively separated and purified, followed by subjecting to quantitative determination. As shown in Table 2, from the culture cells by culturing in the medium to which validamycin A was supplemented, a remarkably increased amount of trehalose was obtained as compared with those by culturing in the medium to which no validamycin A was supplemented.

TABLE 2

| | Influence of validamycin A on the production of trehalose | |
| --- | --- | --- |
| Amount of validamycin A added (%) | Content of trehalose in mycelia (mg/g dry mycelia) | Ratio relative to Control without validamycin A (%) |
| 0 | 80.3 | 100.0 |
| 0.0005 | 108.1 | 134.6 |

EXAMPLE 3

In a 200 ml.-capacity flask was put a 100 ml.-portion of a Czapek's liquid medium in which sucrose was replaced with glucose. The medium was sterilized at 115° C. for 15 minutes. The resultant culture medium was inoculated with a piece of the growth (punched out with a cork borer, diameter 1 cm) of Rhizoctonia solani AG-1 (accession number IFO-30465) cultured on a PSA culture medium at 28° C. for two days and subjected to shake-culture at 28° C. for four days. To the resultant was added validamycin A (0 to 0.0005%), which was cultured for further 2 days. The culture cells obtained thus above were respectively separated and purified by the above-mentioned method, followed by subjecting to quantitative determination. As shown in Table 3, from the culture cells by culturing in the medium to which validamycin A was supplemented, a remarkably increased amount of trehalose was obtained as compared with those by culturing in the medium to which no validamycin A was supplemented.

TABLE 3

| | Influence of validamycin A on the production of trehalose | |
| --- | --- | --- |
| Amount of validamycin A added (%) | Content of trehaloseto in mycelia (mg/g dry mycelia) | Ratio relative to control without validamycin A (%) |
| 0 | 71.2 | 100.0 |
| 0.0001 | 88.7 | 124.6 |
| 0.0002 | 111.1 | 156.1 |
| 0.0005 | 136.3 | 191.4 |
| 0.001 | 132.4 | 186.0 |

EXAMPLE 4

In a 200 ml.-capacity flask was put 100 ml.-portion of a Czapek's liquid medium in which sucrose was replaced with glucose. The medium was sterilized at 115° C. for 15 minutes. The resultant culture medium was inoculated with a piece of the growth (punched out with a cork borer, diameter 1 cm) of strains mentioned in Table 4 cultured on a PSA culture medium at 28° C. for two days and subjected to shake-culture at 28° C. for six days. To the resultant was added validamycin A (0.0005%) and it was cultured for further 2 days. Similarly, the culture medium, to which no validamycin A was added, was cultured for two days. The culture cells obtained thus above were respectively separated and purified by the above-mentioned method, followed by subjecting to quantitative determination. As shown in Table 4, from the culture cells of all the test strains by culturing in the medium to which validamycin A was supplemented, a remarkably increased amount of trehalose was obtained as compared with those by culturing in the medium to which no validamycin A was supplemented.

TABLE 4

Influence of validamycin A on the production of trehalose by Sclerotina sclerotiorum

| Test strain * | Amount of validamycin A (%) | Content of in dry mycelia (mg/g) | Ratio relative to control without validamycin A (%) |
|---|---|---|---|
| 1 | 0 | 88.4 | 100.0 |
|   | 0.0005 | 119.8 | 135.5 |
| 2 | 0 | 66.7 | 100.0 |
|   | 0.0005 | 90.8 | 136.1 |
| 3 | 0 | 51.5 | 100.0 |
|   | 0.0005 | 80.3 | 155.9 |
| 4 | 0 | 62.5 | 100.0 |
|   | 0.0005 | 92.7 | 148.3 |
| 5 | 0 | 58.4 | 100.0 |
|   | 0.0005 | 74.4 | 127.4 |

* 1 Rhizoctonia solani AG-1 (Accession number IFO-30465)
2 Rhizoctonia solani AG-2-2 (Hokkaido Univ. 2-2 III B)
3 Rhizoctonia oryzae (Ministry of Agriculture, Forestry and Fisheries, Central Agricultural Experiment Station C-301)
4 Sclerotium oryzae-sativae (Ministry of Agriculture, Forestry and Fisheries, Central Agricultural Experiment Station C-344)
5 Sclerotium fumigatum (Ministry of Agriculture, Forestry and Fisheries, Central Agricultural Experiment Station)

EXAMPLE 5

In a 200 ml.-capacity flask was put 100 ml.-portion of a Czapek's liquid medium in which sucrose was replaced with glucose. The medium was sterilized at 115° C. for 15 minutes. The resultant culture medium was inoculated with a piece of Rhizoctonia solani (accession number IFO-30465) (punched out with a cork-borer, diameter 1 cm) cultured on a PSA culture medium at 28° C. for two days, which was subjected to shake-culture at 28° C. for six days. To the resultant was added validamycin A (0.0005%), which was cultured for 2 further days. Similarly, the culture medium, to which no validamycin A was added, was cultured for two days. The culture cells obtained thus above were respectively separated and purified by the above-mentioned method, followed by subjecting to quantitative determination. As shown in Table 5, from the culture cells cultured in the medium to which validamycin A or validamycin B was supplemented, a remarkably increased amount of trehalose was obtained as compared with those by culturing in the medium to which no validamycin A was supplemented.

TABLE 5

Influence of validamycin A and validamycin B on the production of trehalose

|  | Amount added (%) | Content of trehalose in dry mycelia (mg/g) | Ratio relative to content without addition (%) |
|---|---|---|---|
| Validamycin A | 0 | 105.3 | 100.0 |
|  | 0.0005 | 149 | 141.6 |
| validamycin B | 0.0005 | 136.5 | 129.6 |

We claim:

1. An industrial scale method for producing trehalose in increased yield which comprises culturing a microorganism capable of producing trehalose selected from the group consisting of, Sclerotium oryzae-sativae and Sclerotium fumigatum, in a culture medium containing an effective amount of validamycin or its derivative whereby trehalose production by said microorganism is promoted, the validamycin or its derivative being represented by the formula

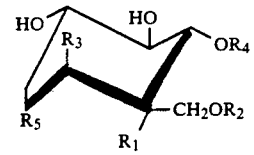

wherein $R_1$ is a hydrogen atom or a hydroxy group; $R_2$ is a hydrogen atom or a D-glucopyranosyl group; $R_3$ is a hydrogen atom or a hydroxy group; $R_4$ is a hydrogen atom, a D-glucopyranosyl group or a D-glucopyranosyl-D-glucopyranosyl group; $R_5$ is a hydrogen atom, an amino group or a substituent of the formula

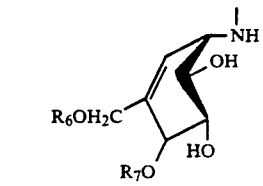

wherein each of $R_6$ and $R_7$ is a hydrogen atom or a D-glucopyranosyl group, or alternatively (2)(1S)-(1,4,6/5)-3-hydroxymethyl-4,5,6-trihydroxy-2-cyclohexenyl amine, and recovering and purifying trehalose.

2. An industrial scale method for producing trehalose comprising:
(a) culturing a microorganism capable of producing trehalose selected from the group consisting of Sclerotium oryzae-sativae and Sclerotium fumigatum, in a culture medium containing an amount of validamycin or its derivative whereby trehalose production by the microorganism is promoted, said validamycin or its derivative being represented by the formula

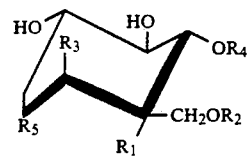

wherein $R_1$ is a hydrogen atom or a hydroxy group; $R_2$ is a hydrogen atom or a D-glucopyranosyl group; $R_3$ is a hydrogen atom or a hydroxy group; $R_4$ is a hydrogen atom, a D-glucopyranosyl group or a D-glucopyranosyl-D-glucopyranosyl group; $R_5$ is a hydrogen atom, an amino group or a substituent of the formula

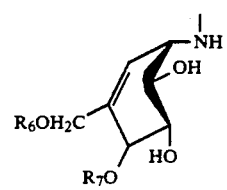

wherein each of $R_6$ and $R_7$ is a hydrogen atom or a D-glucopyranosyl group, or alternatively (2)(1S)-

(1,4,6/5)-3-hydroxymethyl-4,5,6-trihydroxy-2-cyclohexenyl amine, for about 2 to about 10 days;
(b) extracting said trehalose from one of said medium and said microorganism; and
(c) purifying said trehalose.

3. The method of claim 1 in which the validamycin or a derivative thereof is selected from the group consisting of: alienamine, validatol, validamine, valiolamine, validoxylamine A, validoxylamine B, validoxylamine G, validamycin A, validamycin B, validamycin C, validamycin D, validamycin E, validamycin F and validamycin G.

4. The method of claim 1, wherein the amount of validamycin or its derivative is in the range of 0.000001 to 0.01% (W/V) relative to the whole culture medium.

5. The method of claim 1, wherein the amount of validamycin or its derivative is in the range of 0.00001 to 0.002% (W/V) relative to the whole culture medium.

6. The method of claim 1, wherein the said culturing is conducted at a temperature in the range of from about 25° C. to about 35° C.

7. The method of claim 1, wherein the said culture medium is at a pH in the range of from about 5 to about 9.

8. The method of claim 1, wherein said microorganism is *Sclerotium oryzae-sativae* (IFO 32333).

9. The method of claim 1, wherein said microorganism is *Sclerotium fumigatum* (IFO 32332).

10. The method of claim 2, wherein the amount of validamycin or its derivative is in the range of 0.000001 to 0.01% (W/V) relative to the whole culture medium.

11. The method of claim 2, wherein the amount of validamycin or its derivative is in the range of 0.00001 to 0.002% (W/V) relative to the whole culture medium.

12. The method of claim 2, wherein the said culturing is conducted at a temperature in the range of from about 25° C. to about 35° C.

13. The method of claim 2, wherein the said culture medium is at a pH in the range of from about 5 to about 9.

14. The method of claim 2, wherein said extracting step (b) is performed by crushing mycelia of said cultured microorganisms, exposing said crushed mycelia to an acidic solution, filtering said solution, and drying said solution.

15. The method of claim 2, wherein said purifying step (c) is performed by gel chromatography.

16. The method of claim 2, in which the validamycin or a derivative thereof is selected from the group consisting of: valienamine, validatol, validamine, valiolamine, validoxylamine A, validoxylamine B, validoxylamine G, validamycin A, validamycin B, validamycin C, validamycin D, validamycin E, validamycin F and validamycin G.

17. The method of claim 2, wherein said microorganism is *Sclerotium oryzae-sativae* (IFO 32333).

18. The method of claim 2, wherein said microorganism is *Sclerotium fumigatum* (IFO 32332).

* * * * *